(12) United States Patent
Odakura et al.

(10) Patent No.: US 6,773,672 B2
(45) Date of Patent: Aug. 10, 2004

(54) AUTOMATIC ANALYSIS APPARATUS

(75) Inventors: Masaaki Odakura, Naka-machi (JP); Shigenori Watari, Hitachinaka (JP); Yoichiro Suzuki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 483 days.

(21) Appl. No.: 09/814,683

(22) Filed: Mar. 15, 2001

(65) Prior Publication Data

US 2002/0025579 A1 Feb. 28, 2002

(30) Foreign Application Priority Data

Aug. 31, 2000 (JP) ........................................ 2000-263853

(51) Int. Cl.[7] .............................................. G01N 21/01
(52) U.S. Cl. .................... 422/64; 422/82.05; 422/82.08; 422/82.09; 436/164; 436/165; 436/166; 436/172; 436/174
(58) Field of Search ................................ 366/108, 143; 436/164, 165, 166, 172, 174; 422/64, 82.05, 82.08, 82.09

(56) References Cited

U.S. PATENT DOCUMENTS

| | | | | |
|---|---|---|---|---|
| 4,826,319 A | * | 5/1989 | Namba et al. | ............... 356/339 |
| 5,679,581 A | * | 10/1997 | Miyazaki et al. | ............ 436/517 |
| 6,383,452 B1 | * | 5/2002 | Miyake et al. | ................. 422/63 |
| 2001/0019702 A1 | * | 9/2001 | Watari et al. | .................. 422/67 |

FOREIGN PATENT DOCUMENTS

| | | |
|---|---|---|
| JP | 8-146007 | 6/1996 |
| JP | 8-189889 | 7/1996 |
| JP | 9-58941 | 3/1997 |
| JP | 10-123136 | 5/1998 |

* cited by examiner

Primary Examiner—Jan M. Ludlow
(74) Attorney, Agent, or Firm—Mattingly, Stanger & Malur, P.C.

(57) ABSTRACT

In order to provide an automatic analyzer which ensures accurate absorbance measurement even when ultrasonic wave intensity for agitation of the sample and reagent or the like becomes excessive, multiple reaction vessels 8 are placed as follows: As viewed from the top of the reaction disk 15, the reaction disk 15 is divided into four parts, and the side wall of the reaction vessel 8 does not intersect with two light beams 20 which intersect with each other at right angles. Herein multiple reaction vessels 8 are located at an inclined position approximately at an angle of about 45 deg. This layout allows the reaction vessel 8 to have the surface exposed to ultrasonic wave 22 intersecting to the applied ultrasonic wave appropriately at right angles, and absorbance measuring surface 21 intersecting to the applied measurement wave appropriately at right angles. It is possible to configure that the surface exposed to ultrasonic wave 22 and absorbance measuring surface 21 are different surfaces to ensure that this absorbance measuring surface 21 is not be exposed to ultrasonic wave.

8 Claims, 3 Drawing Sheets

AUTOMATIC ANALYSIS APPARATUS

BACKGROUND OF THE INVENTION

The present invention relates to the automatic analyzer to analyze components of a sample using a reagent or the like, and particularly to automatic analyzer ensuring improved efficiency of agitation between said reagent or the like and sample.

Techniques used in the agitator of the prior automatic analyzer include the method of inserting a spatula-shaped agitating rod directly in the reaction vessel and giving it rotation or reciprocating motion, thereby conducting agitation between the sample and reagent or the like, and the method disclosed in the Japanese Official Patent Gazette 038011/1991 where agitation is accomplished by tilting and rotating the reaction vessel.

Other known methods include the method disclosed in the Japanese Official Patent Gazette 123136/1998 where the reagent itself is synthesized with magnetic magnetic particulates and agitation is performed by external magnetism, and the method disclosed in the Japanese Official Patent Gazette 189889/1996 where a barrier is provided in the reaction vessel and a clearance is provided on the bottom of said reaction vessel to allow free passage of liquid so that agitation can be performed by pneumatic pressure.

However, in the method of inserting a spatula-shaped agitation rod into the reaction vessel, a phenomenon called carry-over occurs where reagent or sample deposited on the agitation rod affects the result of the following analyses, if a sufficient washing of the agitation rod cannot be ensured.

To solve this problem, vibration is applied to the agitation to assist removal of the sample or reagent deposited on the agitation rod, as disclosed in Japanese Official Patent Gazette 58941/1994.

The method of applying vibration to the agitation rod requires a sufficient opening area of the reaction vessel to insert the agitation rod and to provide agitation or reciprocating motion. This requires a reaction vessel of a large capacity, and the amount of the sample stored in this big reaction vessel must be increased.

If the amounts of sample and reagent are reduced in order to reduce the physical load of the sample provider and to reduce the running cost of the equipment, light must be measured close to the bottom of the reaction vessel when optical measurement is conducted. To maintain accuracy of measurement close to the bottom of the reaction vessel, the reaction vessel must be provided with special processing.

For this reason, the method of giving vibration to agitation rod results in increased costs. This is not preferred from the view point of cost reduction.

In the method of mixing and agitation of the sample and reagent or the like by tilting and rotating the reaction vessel, solution is likely to scatter a splash of solution may be mixed with other objects to be analyzed.

The method of using reagent including magnetic particulates requires reagent to be developed, and this raises cost problems.

The method of installing a barrier to the reaction vessel to provide agitation through pneumatic pressure requires the reaction vessel to be subjected to special processing, and this also involves cost problems.

A method is disclosed and claimed in Japanese Official Patent Gazette 146007/1996. The technique in this Gazette uses ultrasonic wave to agitate the sample and reagent or the like. It allows the sample and reagent or the like to be agitated without being touched by other substances. It does not contaminate other samples and reagents or the like, and does not require use of an agitation rod. This makes it possible to reduce the size of the reaction vessel and to decrease the amount of sample and reagent.

As described above, use of ultrasonic wave for agitation of the sample and reagent or the like in the agitator of the automatic analyzer allows agitation to be performed without touching the sample and reagent or the like, and does not contaminate other samples and reagents or the like. In addition, since no agitation rod is used, it is possible to reduce the size of the reaction vessel and to decrease the amounts of the sample and reagent.

However, if excessive ultrasonic wave intensity is used for agitation, the portion of the reaction vessel wall allowing sound wave to pass by will be heated when ultrasonic wave is applied with few solution specimens or no specimens at all in the reaction vessel. This may cause the surf ace of the reaction vessel to be distorted, depending on the materials.

This may dampen the amount of light which is applied for absorbance measurement and which passes through the reaction vessel, and may lead to failure in accurate absorbance measurement.

There are a great varieties reagents used for colorimetric analysis. When ultrasonic wave of the same intensity is applied, fluidity is more likely to occur, and mixing capacity is higher if the reagent having greater wettability with the reaction vessel is used.

This requires ultrasonic wave intensity to be set for each reagent. It is necessary to monitor the state of agitation, namely, absorbance measurements in real time, and to set up ultrasonic wave intensity. The reagent vessel must be moved to the light measuring position to conduct absorbance measurement every time. These steps are quite complicated, and much time must be used for absorbance measurement.

SUMMARY OF THE INVENTION

The object of the present invention is to provide an automatic analyzer that ensures accurate absorbance measurement even if ultrasonic wave intensity becomes excessive for agitation of sample and reagent or the like.

Another object of the present invention is to provide an automatic analyzer which ensures accurate absorbance measurement even when ultrasonic wave intensity for agitation of the sample and reagent or the like becomes excessive, and which allows optimization of the ultrasonic wave intensity in a short time.

To achieve said object, the present invention has the following composition:

(1) An automatic analyzer comprising;
    a reaction vessel where solution specimen is mixed with reagent to react with it,
    a light source to apply light to said reaction solution and
    an analysis unit to analyze light passing through said reaction solution;
    wherein said automatic analyzer further comprises an agitator to apply ultrasonic wave to said reaction solution and to agitate said reaction solution, and
    the direction of the ultrasonic wave emitted from said agitator and the direction of the light applied to said reaction solution are deviated from each other by at least the size of the spot irradiated by ultrasonic wave.

When the ultrasonic wave applied to the surface exposed to ultrasonic wave is excessive, the spot surface of the reaction vessel exposed to the ultrasonic wave may be deformed by heat generation or the like. If the surface of the deformed reaction vessel overlaps the surface exposed to the light passing through the reaction solution (absorbance measuring surface), then correct measurement may not be obtained.

As described above, if the surface exposed the light passing through the reaction solution does not overlap the spot exposed to ultrasonic wave, no error occurs to the result of the measurement. This makes it possible to produce an automatic analyzer which ensures accurate measurement of absorbance despite excessive intensity of ultrasonic wave due to agitation between sample and reagent.

The direction of deviation can be either vertical or lateral.

(2) An automatic analyzer comprising;
a reaction vessel where solution specimen is mixed with reagent to react with it,
a light source to apply light to said reaction solution and
an analysis unit to analyze light passing through said reaction solution;
wherein said automatic analyzer further comprises an agitator to apply ultrasonic wave to said reaction solution and to agitate said reaction solution, and
ultrasonic wave coming from said agitator and light applied to said reaction solution can be emitted simultaneously.

This composition allows the state of agitation to be monitored further on the real-time basis by means of the measurement of light, so the optimization of agitation conditions is facilitated.

(3) In (1) described above, said reaction vessel may have a form of prism and the surface exposed to ultrasonic wave emitted from said agitator may be different from the surface exposed to light applied to said reaction solution.

The reaction vessel can be shaped like either a cylinder or prism. If it has a form of prism, the direction of the light applied to reaction solution can be easily deviated from the direction of the ultrasonic wave emitted by at least the size of the spot irradiated by ultrasonic wave by changing the prism-formed surface exposed to ultrasonic wave and the prism-formed surface exposed to light. For example, when a prism-formed reaction vessel is used, the angle of irradiation can be deviated 90 deg.

(4) In (2) described above, irradiation conditions of ultrasonic wave coming from said agitator can be controlled, based on the result of analyzing the light passing through said reaction solution.

(5) In (4) described above, the reagent for agitation and regulation can be used to analyze the light passing through reaction solution and to determine the optimum irradiation conditions of ultrasonic wave.

(6) In (5) described above, said optimum irradiation conditions of ultrasonic wave can be stored in memory and ultrasonic wave irradiation conditions can be determined in the analysis using the reagent other than that for agitation and regulation, based on said irradiation conditions.

DETAILED DESCRIPTION OF THE PREFERRED EMBODIMENT

Figure 1:
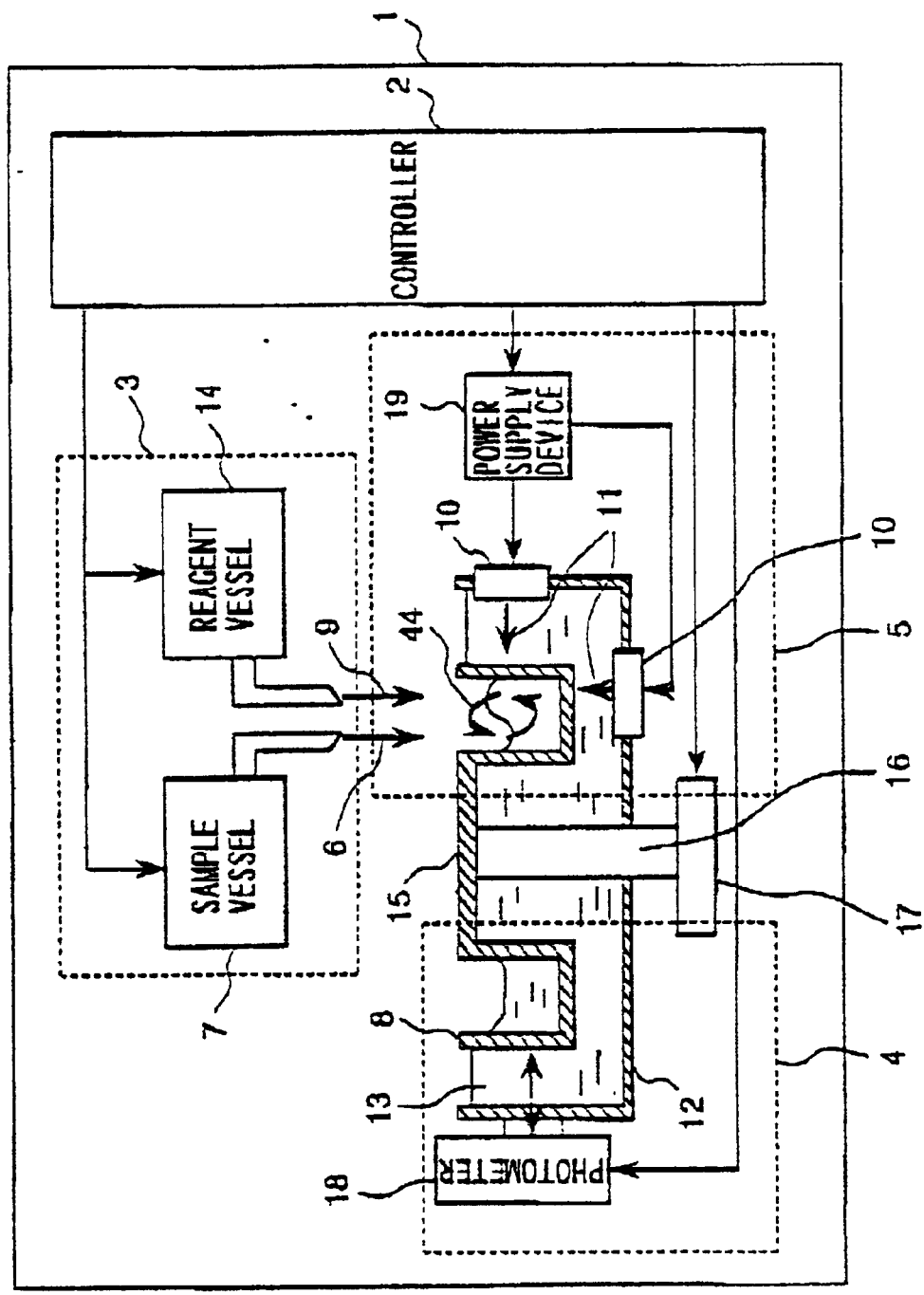
FIG. 1 is a schematic diagram of an automatic analyzer representing one embodiment of the present invention.
Figure 2:
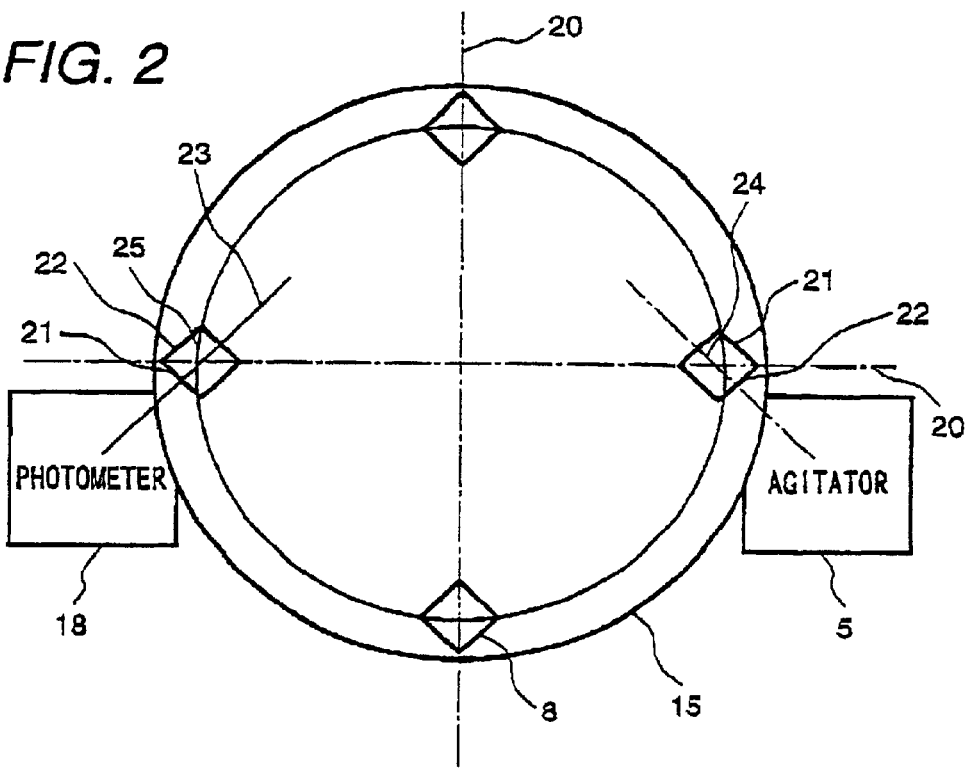
FIG. 2 is a top view of the reaction disk in the first embodiment of the present invention.

The following describes the embodiments according to the present invention in details with reference to drawings:

FIG. 1 is a schematic diagram of an automatic analyzer representing a first embodiment of the present invention. FIG. 2 is a top view of the reaction disk 15 in the first embodiment of the present invention.

In FIGS. 1 and 2, the automatic analyzer 1 comprises a controller 2, storage device 3, analyzer 4, and agitator 5.

The controller 2 consists of an electronic circuit to provide detailed operation control of each section and a storage device, and controls system operations.

The storage device 3 consists of a sample storage device 7 containing sample 6 and a reagent storage device 14 containing reagent 9.

The agitator 5 agitates the sample 6 discharged from the sample storage device 7 to the reaction vessel 8 and the reagent 9 discharged from the reagent storage device 14 to the reaction vessel 8, using the circulating flow 44 based on the effect of acoustic radiation pressure due to ultrasonic wave 11 generated by a piezoelectric element 10.

The piezoelectric element 10 is installed below or above the reaction vessel 8 to apply ultrasonic wave 11 from below to raise the liquid surface of the mixture of sample 7 and reagent 9. After that, ultrasonic wave 11 is applied to the raised portion of the liquid surface from the side, and circulating flow 44 by acoustic radiation pressure is produced to perform agitation.

The agitator 5 and reaction vessel 8 located in the analyzer 4 are immersed in heat insulation medium 13 represented by water stored in the reaction tank 12, thereby keeping a constant temperature.

These multiple reaction vessels 8 are laid out on the reaction disk 15, and are connected to the reaction disk motor 17 by means of reaction disk shaft 16.

Reaction disk motor 17 is rotated or moved together with reaction disk 15 through control by the controller 2 to make a reciprocating motion between agitator 5 and spectroscope 18. Analysis device 4 mixes and reacts the sample 6 with reagent 9 in the reaction vessel 8 of this analysis device 4, and the composition is analyzed by spectroscope 18.

At agitating position 24, the sample discharged from the sample storage device 7 to the reaction vessel 8 and reagent 9 discharged from the reagent storage device 14 to the reaction vessel 8 are agitated by ultrasonic wave 11 generated by the piezoelectric element 10.

Multiple reaction vessels 8 are placed as follows: As viewed from the top of the reaction disk 15, the reaction disk 15 is divided into four parts, and the side wall of the reaction vessel 8 does not intersect with two light beams 20 which intersect with each other at right angles. Herein multiple reaction vessels 8 are located at an inclined position approximately at an angle of about 45 deg.

According to this layout, the reaction vessel 8 has the surface exposed to ultrasonic wave 22 intersecting to the applied ultrasonic wave appropriately at right angles, and absorbance measuring surface 21 intersecting to the applied measurement wave appropriately at right angles. To prevent this absorbance measuring surface 21 from being exposed to ultrasonic wave, the agitator 5 and photometer 18 can be laid out.

Upon completion of agitation of the specimen by agitator 5, the reaction disk 15 rotates and the reaction vessel 8 moves to the light measuring position 25. Then absorbance measurement is carried out by a photometer.

As described above, multiple reaction vessels 8 according to the first embodiment of the present invention are placed as follows: As viewed from the top of the reaction disk 15, the reaction disk 15 is divided into four parts, and the side wall of the reaction vessel 8 does not intersect with two light beams 20 which intersect with each other at right angles. Herein multiple reaction vessels 8 are located at an inclined position approximately at an angle of about 45 deg.

This layout allows the reaction vessel 8 to have the surface exposed to ultrasonic wave 22 intersecting to the applied ultrasonic wave appropriately at right angles, and absorbance measuring surface 21 intersecting to the applied measurement wave appropriately at right angles. It is possible to configure that the surface exposed to ultrasonic wave 22 and absorbance measuring surface 21 are different surfaces to ensure that this absorbance measuring surface 21 is not be exposed to ultrasonic wave.

Thus, even if the surface exposed to ultrasonic wave 22 is deformed due to an excessive intensity of ultrasonic wave applied thereto, the absorbance measuring surface 21 is not exposed to ultrasonic wave; therefore, it can be prevented from being deformed by ultrasonic wave.

Thus, the present invention provides an automatic analyzer which ensures accurate measurement of absorbance even if there is an excessive intensity of ultrasonic wave for agitation of the sample and reagent or the like.

Figure 3:
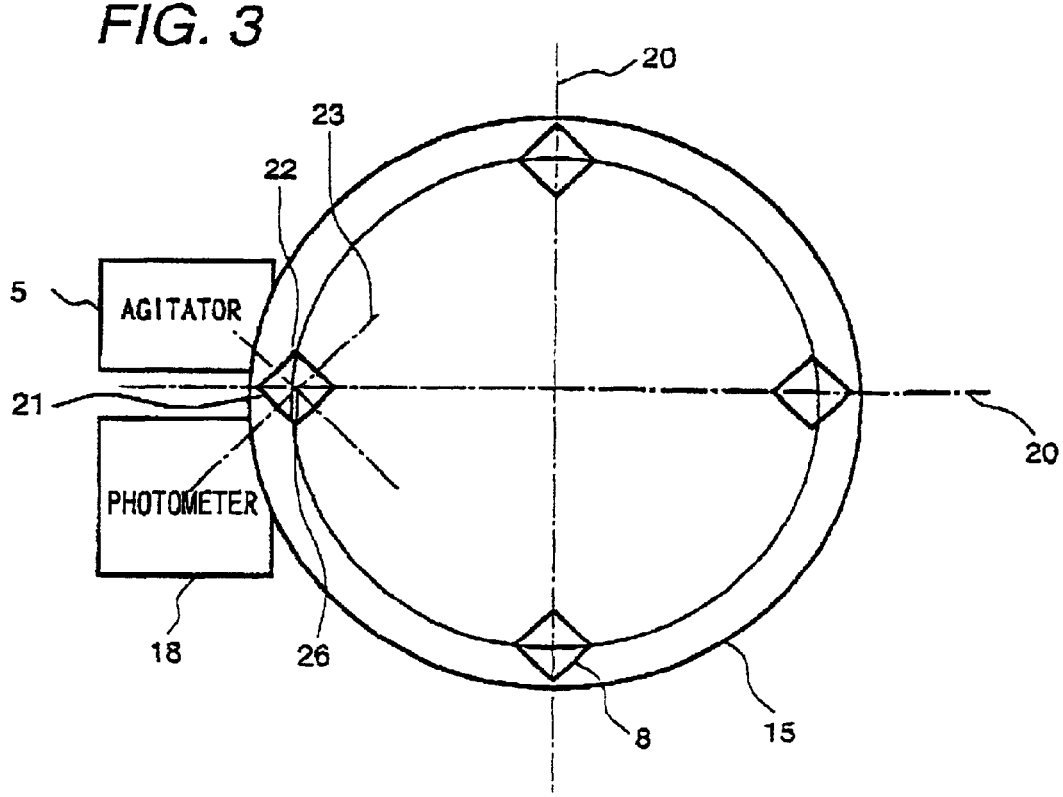
FIG. 3 is a top view representing the reaction disk of an automatic analyzer as the second embodiment of the present invention.

FIG. 3 is a top view representing the reaction disk 15 of an automatic analyzer as the second embodiment of the present invention.

The following describes the second embodiment according to the present invention with reference to FIGS. 1 and 3:

In the above-mentioned first embodiment, the agitating position 24 of the reaction vessel 8 and light measuring position 25 are separate from each other on the reaction disk 15.

In the second embodiment according to the present invention, by contrast, mechanisms are designed to ensure that agitation of solution specimen stored in the reaction vessel 8 and absorbance measurement are performed at one and the same position on the reaction disk 15.

To be more specific, agitator 5 and photometer 18 are arranged to ensure that ultrasonic wave 11 is applied to the surface exposed to ultrasonic wave 22 of the reaction vessel 8 from the agitator 5 at the agitating/light measuring position 26 on the reaction disk 15; and at the same time, light for absorbance measurement coming from the photometer 18 can be applied to the absorbance measuring surface 21 of the reaction vessel 8.

Agitation according to the above-mentioned method allows the state of agitation to be monitored on real-time basis.

Other configuration is the same as that shown in FIGS. 1 and 2, and detailed explanation will be omitted.

In FIGS. 1 and 3, the sample 6 discharged from the sample storage device 7 to reaction vessel 8 and the reagent 9 discharged from the reagent storage device 14 to the reaction vessel 8 as the specimen to be measured are fed to the agitating/light measuring position 26 by the rotation of the reaction disk 15.

The controller 2 sends the trigger signal to generate ultrasonic wave 11 and the trigger signal is applied to the piezoelectric element 10 through this power supply device 19.

The piezoelectric element 10 applies the ultrasonic wave 11 proportional to the voltage intensity and frequency supplied from the power supply device 19 to the reaction vessel 8, and agitates the solution specimen.

In the method of using a spatula conventionally employed in general cases, it is difficult to install an agitation mechanism at the position physically adjacent to the photometer 18. Even if the agitation mechanism can be installed adjacent to the photometer 18, the state of agitation cannot be monitored simultaneously with agitating operation since the spatula is inserted into the reaction vessel 8 for agitation.

According to the second embodiment of the present invention, the agitator 5 which employs ultrasonic wave 11 is used for agitation. This allows the controller 2 to make simultaneous checking of both agitation and monitoring of absorbance data sent from photometer 18 showing the state of agitation.

As described above, according to the second embodiment of the present invention, it is possible to provide an automatic analyzer which ensures accurate measurement of absorbance even if there is an excessive intensity of ultrasonic wave for agitation of the sample and reagent or the like, and to permit the optimum ultrasonic wave intensity to be set in a short time.

The following describes the third embodiment according to the present invention with reference to FIG. 1:

The third embodiment is based on the configuration of the first and second embodiments.

Reaction between the specimen and reagent is commonly called color comparison reaction. As the name implies, absorbance changes in the specific range of wavelength. With the increased concentration of measured components in the specimen, there is an increase in the amount of absorbed light having the wavelength most seriously affected by the absorption of light, and a decrease in the amount of light entering the corresponding light detector.

Thus, said reagent for agitation and adjustment is prepared to measure absorbance of the specimen obtained by agitating the reagent and sample (distilled water or degassified water). The absorbance is determined by the amount of of the dispensed reagent and sample, so the controller 2 stores that value as a reference value.

After that, to reach that absorbance, the controller 2 compares the result of absorbance measurement sent from the photometer 18 and reference value on real-time basis to evaluate if the agitating operation of the agitator 5 is sufficient or not. If agitation is insufficient, it changes the intensity of the trigger signal to generate ultrasonic wave 11.

Thus, ultrasonic wave intensity also changes in proportion. Ultrasonic wave intensity is changed until measured absorbance reaches the reference value or the optimum state of agitation, thereby allowing the optimum ultrasonic wave intensity to be set.

Further, if the reference value cannot be reached by changing ultrasonic wave intensity is changed, the agitator 5 or the optical system including the photometer 18 may be in trouble. In this case, a buzzer can be installed to alert the operator.

As described above, the automatic analyzer according to third embodiment of the present invention has the same configuration as that of said first embodiment or second embodiment, and is designed to agitate said reagent for agitation and adjustment and sample and to set the ultrasonic wave intensity. This makes it possible to get the same effect to that of said first or second embodiment. In addition, this automatic analyzer allows the optimum ultrasonic wave intensity to be set in a short time.

Figure 4:
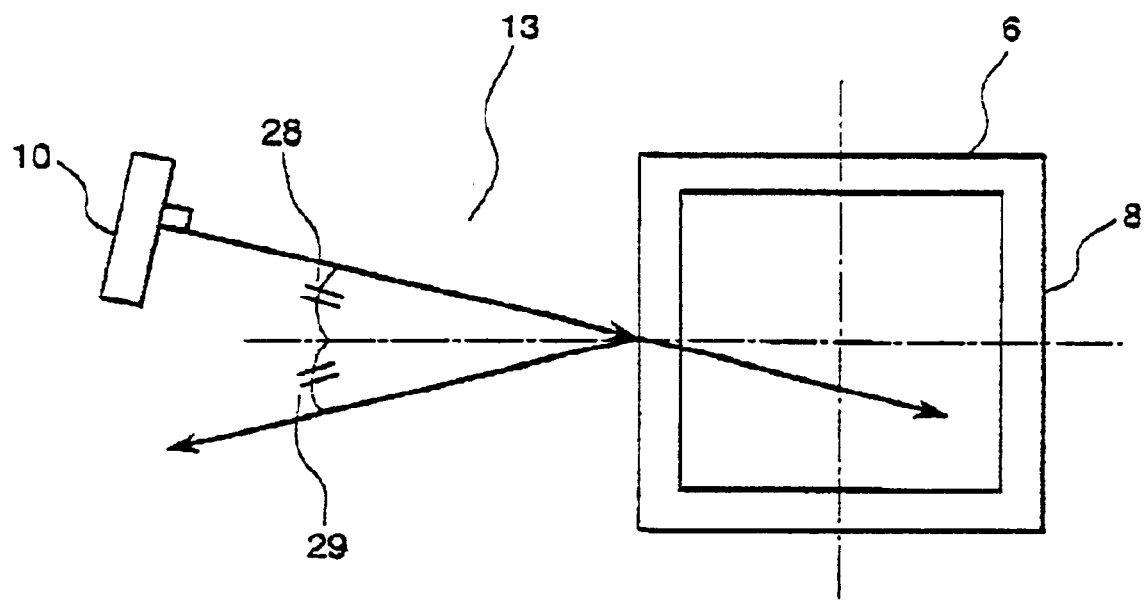
FIG. 4 is a drawing representing the positional relation between an ultrasonic wave transmitter and reaction vessel of the automatic analyzer in the fourth embodiment of the present invention.

The following describes the fourth embodiment of the present invention with reference to FIG. 4: FIG. 4 shows the top view close to the piezoelectric element (10) incorporated in the reaction disk (1S). Ultrasonic wave emitted from the piezoelectric element (10) is applied at an included angle to the surface of the reaction vessel (8). This incident angle of ultrasonic wave (28) is an angle where ultrasonic wave reflected from the surface for application of ultrasonic wave to the reaction vessel does not come back to the piezoelectric element (10).

For ultrasonic wave reflection angle (29), the reflection factor differs according to the density of heat insulation medium (13) which maintain the temperature of the reaction vessel (8). Since distilled water is mainly used as this heat insulation medium (13), reflection occurs at almost the same angle as ultrasonic wave incident angle (28).

Ultrasonic wave can be divided into two types; ultrasonic wave passing through the reaction vessel and reflected ultrasonic wave. Ultrasonic wave passing through the reaction vessel is used to agitate the sample. However, if the piezoelectric element is arranged where reflected wave comes back, this reflected wave may affect the piezoelectric element. In this case, the controller provides control to ensure that the control signal given to the piezoelectric element has the frequency and signal intensity allowing agitation. However, this results in a complicated control due to the influence of reflected wave. To overcome this problem, the piezoelectric element is placed where reflected wave does not come back.

When the reaction vessel is shaped in a polygonal column, reflected wave does not come back to the piezoelectric element if arrangement is made to ensure the surface projected vertically toward the ultrasonic wave transmitter from the surface of the reaction vessel exposed to ultrasonic wave does not overlap the piezoelectric element of the ultrasonic wave transmitter.

In the above-mentioned embodiment, multiple reaction vessels 8 are placed as follows: As viewed from the top of the reaction disk 15, the reaction disk 15 is divided into four parts, and the side wall of the reaction vessel 8 does not intersect with two light beams 20 which intersect with each other at right angles. Herein multiple reaction vessels 8 are located at an inclined position approximately at an angle of about 45 deg. If the agitator 5 applies ultrasonic wave to the surface exposed to ultrasonic wave of the reaction vessel 8, and measurement light from the light source is applied to the surface exposed to measurement light located at the different position from the surface exposed to ultrasonic wave of the reaction vessel 8, it is possible to arrange the side walls of reaction vessels 8 to intersect with light beam 20 approximately at right angles.

In the above-mentioned example, the reaction vessel 8 has a form of a prism, but is not restricted thereto. Use of a circular form may be acceptable to the present invention.

The automatic analyzer according to the present invention has an ultrasonic generating source used in the agitator of this analyzer and is characterized in that reaction vessels are placed at an inclined position to the reaction disk. The present invention has the following effects:

The reaction vessel has an surface exposed to ultrasonic wave separately from an absorbance measurement surface. As a result, ultrasonic wave is not applied to the absorbance measuring surface, and excessive amount of ultrasonic wave is applied to the surface exposed to ultrasonic wave. Even if the surface exposed to ultrasonic wave has undergone deformation, the absorbance measuring surface is not exposed to ultrasonic wave, thereby avoiding the possibility of deformation.

Thus, the present invention provides an automatic analyzer which ensures accurate measurement of absorbance even if there is an excessive intensity of ultrasonic wave for agitation of the sample and reagent or the like.

Further, agitation and measurement of light are performed at one and the same position. This provides an automatic analyzer ensuring accurate measurement of absorbance even if there is an excessive intensity of ultrasonic wave for agitation of the sample and reagent or the like. At the same time, said analyzer permits the optimum ultrasonic wave intensity to be set in a short time.

Use of said reagent for agitation and adjustment provides an automatic analyzer allowing the optimum ultrasonic wave intensity to be set in a short time.

What is claimed:

1. An automatic analyzer comprising;
   a reaction vessel having a prismatic shape in which a solution specimen is mixed with a reagent to react therewith,
   a reaction disk which holds a plurality of said reaction vessels thereon,
   a light source to apply light to said reaction solution, and
   an analysis unit to analyze light passing through said reaction solution;
   wherein said automatic analyzer further comprises an agitator to apply ultrasonic waves to said reaction solution and to agitate said reaction solution, and
   wherein the direction of the ultrasonic waves emitted from said agitator and the direction of the light applied to said reaction solution are deviated from each other to the extent to which the surface exposed to ultrasonic waves on said reaction vessel does not overlap the surface exposed to light and said surfaces of said reaction vessels are located substantially at an angle of 45 degrees relative to a radial direction of said reaction disk.

2. An automatic analyzer according to claim 1 wherein
   the surface exposed to ultrasonic waves on said reaction vessel has a size formed by projecting the size of the electrode surface of the ultrasonic wave transmitter of said agitator into the surface of said reaction vessel, while the surface exposed to light has a size formed by projecting on the surface of said reaction vessel the size of the lens which the light emitted from the light source last passes through.

3. An automatic analyzer according to claim 1, wherein said surface exposed to ultrasonic waves is a side surface of said reaction vessel.

4. An automatic analyzer comprising;
   a reaction vessel having a prismatic shape where a solution specimen is mixed with reagent to react therewith,
   a reaction disk which holds a plurality of said reaction vessels thereon,
   a light source to apply light to said reaction solution and
   an analysis unit to analyze light passing through said reaction solution;
   wherein said automatic analyzer further comprises an agitator to apply ultrasonic waves to said reaction solution and to agitate said reaction solution,
   wherein ultrasonic waves coming from said agitator and light applied to said reaction solution can be emitted simultaneously, and
   wherein surfaces of said reaction vessels are located substantially at an angle of 45 degrees relative to a radial direction of said reaction disk.

5. An automatic analyzer according to claim 4, wherein irradiation conditions of ultrasonic waves coming from said agitator are controlled, based on the result of analyzing the light passing through said reaction solution.

6. An automatic analyzer according to claim 4, wherein a reagent for agitation and regulation can be used to analyze the light passing through reaction solution and to determine the optimum irradiation conditions of ultrasonic waves.

7. An automatic analyzer according to claim 6, wherein said optimum irradiation conditions of ultrasonic waves are stored in a memory and ultrasonic wave irradiation conditions are determined in the analysis using a reagent other than that for agitation and regulation, based on said irradiation conditions.

8. An automatic analyzer according to claim 4, wherein said surface exposed to ultrasonic waves is a side surface of said reaction vessel.

* * * * *